United States Patent [19]

Gebauer et al.

[11] Patent Number: 4,647,406

[45] Date of Patent: Mar. 3, 1987

[54] 2-ETHYL-2-PRENYL-3-HEXENOL ITS PREPARATION AND USE AS A FRAGRANT

[75] Inventors: Helmut Gebauer, Munich; Hans Mehlin, Neuried, both of Fed. Rep. of Germany

[73] Assignee: Consortium fur Elketrochemische Industrie GmbH, Munich, Fed. Rep. of Germany

[21] Appl. No.: 781,204

[22] Filed: Sep. 27, 1985

Related U.S. Application Data

[63] Continuation of Ser. No. 639,499, Aug. 10, 1984, abandoned.

[30] Foreign Application Priority Data

Nov. 17, 1983 [DE] Fed. Rep. of Germany ....... 3341604

[51] Int. Cl.⁴ ..................... C07C 29/14; C07C 33/02; A61K 7/46

[52] U.S. Cl. .................. 252/522 R; 568/880; 568/909.5; 568/917

[58] Field of Search ..................... 568/840; 252/522 R

[56] References Cited

U.S. PATENT DOCUMENTS

| | | | |
|---|---|---|---|
| 3,463,818 | 8/1969 | Blumenthal | 568/840 |
| 3,872,172 | 3/1975 | Bertele et al. | 568/840 |
| 3,959,396 | 5/1976 | Ochsner et al. | 568/840 |
| 4,010,207 | 3/1977 | Hall et al. | 568/458 |
| 4,368,145 | 1/1983 | Licciardello et al. | 252/522 R |
| 4,380,675 | 4/1983 | Gebauer et al. | 568/840 |

*Primary Examiner*—J. E. Evans
*Attorney, Agent, or Firm*—Collard, Roe & Galgano

[57] ABSTRACT

The invention relates to 2-ethyl-2-prenyl-3-hexenol, its preparation by the reduction of 2-ethyl-2-prenyl-3-hexenal, and its use as an aromatic substance by itself or as an ingredient in cosmetic compositions.

3 Claims, No Drawings

2-ETHYL-2-PRENYL-3-HEXENOL ITS PREPARATION AND USE AS A FRAGRANT

This application is a continuation of application Ser. No. 639,499 filed Aug. 10, 1984, now abandoned.

The present invention relates to 2-ethyl-2-prenyl-3-hexenol, its preparation and use as a fragrant substance.

From U.S. Pat. No. 4,010,207, the substance 2-ethyl-2-prenyl-3-hexenal has become known as a fragrant substance. The aroma is described as green and sweet with notes of tomatoes, citrus fruits and roses.

In 2-ethyl-2-prenyl-3-hexenol another fragrant substance has been found whose aroma is surprisingly defined by tart and woody notes, the scent being well adapted to blend with compositions of perfumes typically used in men's cosmetics. Moreover, due to its stability in acidic as well as alkaline media, the fragrant substance is useful in a much broader range of products than the chemically less stable aldehyde.

Thus, the primary subject of the present invention is 2-ethyl-2-prenyl-3-hexenol. However, the invention also relates to the production of this novel substance.

In particular, the production is brought about by the reduction of the aldehyde 2-ethyl-2-prenyl-3-hexenal. Examples of suitable reducing agents are complex hydrides, such as sodium boranate, lithium alanate, and aluminum isopropylate (reduction according to Meerwein/Ponndorf).

A preferred method for the production of 2-ethyl-2-prenyl-3-hexenol is characterized by reacting 2-ethyl-2-prenyl-3-hexenal with aluminum isopropylate. The amount of aluminum isopropylate is 0.05–1 mole per mole of the aldehyde to be reacted.

Preferably, the procedure to be followed consists in adding, in doses, the aldehyde to a solution of aluminum isopropylate in isopropanol, while maintaining reaction temperatures at which the acetone obtained as by-product (or a mixture of isopropanol and acetone, respectively) will be distilled off.

The aldehyde used as starting product is preferably obtained in a one-pot process by reaction of butyric aldehyde with prenyl chloride in an organic/alkaline 2-phase system in the presence of a phase transfer catalyst. Under these conditions of reaction, the formation of the aldol condensation product of the butyric aldehyde occurs with simultaneous prenylation of the product in α-position to the aldehyde group.

About 2 moles of butyric aldehyde are used per mole of prenyl chloride. The organic/alkaline 2-phase system is formed by an organic inert solvent, immiscible with water, and an alkali metal hydroxide either in a 5–50% aqueous solution or in solid form.

As phase transfer catalysts, e.g., crown ethers or quaternary ammonium or phosphonium salts are used in amounts of 0.5–5 mole % relative to the prenyl chloride.

The reaction temperatures range from 20°–150° C., and, preferably 60°–70° C.

Preferably, the process is carried out by first introducing the 2-phase system with the catalyst, and a mixture of the reactants is then added drop by drop.

The above-described synthesis procedure is the preferred process for the production of 2-ethyl-2-prenyl-3-hexenol, which is characterized by:

(a) reacting butyric aldehyde and prenyl chloride in a one-pot process in an organic/alkaline 2-phase system in the presence of a phase transfer catalyst; and, (b) reducing the aldehyde obtained in (a) in the presence of aluminum isopropylate.

With 2-ethyl-2-prenyl-3-hexenol a fully synthetic perfume is available from base chemicals, which has an intensive green-woody aroma combined with an amber-like tart aromatic character strongly reminiscent of vetiveria. The scent blends advantageously with patschouli, oak-moss products, lavender, ionone, opoponax and others.

The scenting agent obtained according to the invention is used in the perfumery industry for making cosmetic and technical products. Its aroma is especially suitable for perfumes for men and stresses the woody and balsamic secondary notes.

The invention will not be fully described in a number of examples, but it should be understood that these are given by way of illustration and not of limitation. The figures mentioned with reference to aromatic ingredients are to be understood as parts by weight.

EXAMPLE 1

Preparation of 2-ethyl-2-prenyl-3-hexenol

Into a 2 liter four-neck flask, provided with stirrer, column, dropping funnel, and thermometer, 0.5 moles of aluminum isopropylate and 1 liter of dry isopropanol are first introduced. To the boiling mixture, a solution of 1 mole 2-ethyl-2-prenyl-3-hexenal, dissolved in 200 ml of dry isopropanol were added drop by drop. At all times, the reaction mixture was kept boiling to the extent that the acetone being formed could be withdrawn by the column. When in the distillate acetone could no longer be detected, the isopropanol was distilled off. Finally, the residue was poured into 250 ml of 20% hydrochloric acid, the phases were separate, and the organic phase was dried with calcium chloride. The desired product was then distilled over a Vigreux column.

Boiling point: 95° C. to 0.8 mbar. Yield: 280 g corresponding to 95% of the theoretical.

EXAMPLE 2

"Wood Base"

|  | a | b |
|---|---|---|
| Cypress Oil | 60 | 60 |
| Verdyl acetate (Givaudan Corp.) | 160 | 160 |
| Sandalwood Oil | 140 | 140 |
| Bornyl acetate | 40 | 40 |
| Benzyl acetate | 20 | 20 |
| Tree Moss Colorless abs. | 50 | 50 |
| Patschouli Oil | 50 | 50 |
| Linalyl acetate | 80 | 80 |
| Eugenol | 30 | 30 |
| Labdanum Oil (French) | 20 | 20 |
| Citronell Oil | 30 | 30 |
| Bergamot Oil | 20 | 20 |
| Linalool | 110 | 110 |
| 6-Methyl-α-Ionone | 60 | 60 |
| 2-Ethyl-2-prenyl-3-hexenol | — | 130 |
|  | 870 | 1000 |

The composition has a soft aroma a of noble woods. By the addition of 130 parts by weight of the fragrant substance according to the invention, the aroma becomes rounder and warmer. The balsam-like note of the tree resin is stressed, the newly acquired amber-character imparts to the base a valuable aroma.

EXAMPLE 3

Lavender oil, artificial

|  | a | b |
| --- | --- | --- |
| Lavender Oil | 450 | 450 |
| Lavender Barreme | 100 | 100 |
| Spike Oil (Spanish) | 100 | 100 |
| Bergamot Oil | 50 | 50 |
| Labdanumol (French) | 30 | 30 |
| Oak Moss Extract | 12 | 12 |
| Citronel oil | 18 | 18 |
| Cumarin | 13 | 13 |
| Ketone-Musk | 12 | 12 |
| Nerol | 10 | 10 |
| Indol, 10% solution | 3 | 3 |
| Linalool | 45 | 45 |
| Terpinyl acetate | 95 | 95 |
| 2-Ethyl-2-pyrenyl-3-hexenol | — | 62 |
|  | 938 | 1000 |

The composition has a fresh, herbaceous aroma with balsamic secondary notes. By addition of 62 parts of the compound according to the invention, the herbaceous, slightly camphorous note becomes softer. The balsamic, secondary notes are stressed.

EXAMPLE 4

Stability Test 2-ethyl-2-prenyl-3-hexenol was stored in different media for 60 days at 40° C. Thereupon, the specimens were tested for changes in color and odor, and compared with freshly prepared samples. Moreover, the solutions were studied by means of thin-layer chromatography.

Each test was repeated 4 times. 0.5% by weight solutions of 2-ethyl-2-prenyl-3-hexenol in 60% by weight of aqueous ethanol were prepared and brought to the desired pH values by addition of 0.1 n HCl and 0.1 n NaOH, respectively.

Test solution #1, pH=2
Test solution #2, pH=7
Test solution #3, pH=13

Under the conditions described above, 2-ethyl-2-prenyl-3-hexenol remained stable in all test solutions; no changes in color or aroma could be detected. The thin-layer chromatograms did not indicate any chemical changes.

Comparison Example 1

The method of testing as in Example 4 was repeated with the difference that instead of 2-ethyl-2-prenyl-3-hexenol the scenting agent known from the art, 2-ethyl-2-prenyl-3-hexenal was tested. Result: The comparison compound is stable at pH=7. In alkaline solution (pH=13), there occurred yellow-brown discoloration already after one day and in acidic solution after three days (pH=2). The aroma was clearly changed. In the thin-layer chromatogram, the comparison with a freshly prepared sample showed the presence of foreign matter.

While only several examples of the present invention have been described, it is obvious that many changes and modificatons may be made thereunto, without departing from the spirit and scope of the invention.

What is claimed is:

1. 2-ethyl-2-prenyl-3-hexenol.
2. A compound useful in the cosmetics and perfumery industries consisting entirely of 2-ethyl-2-prenyl-3-hexenol.
3. A composition comprising as a fragrant substance an effective amount of 2-ethyl-2-prenyl-3-hexenol.

* * * * *